US007964339B2

(12) United States Patent
Scott et al.

(10) Patent No.: US 7,964,339 B2
(45) Date of Patent: Jun. 21, 2011

(54) COLD STORAGE OF MODIFIED PLATELETS

(75) Inventors: Mark D. Scott, Surrey (CA); Elisabeth Maurer, Vancouver (CA)

(73) Assignee: Canadian Blood Services (CA)

( * ) Notice: Subject to any disclaimer, the term of this patent is extended or adjusted under 35 U.S.C. 154(b) by 650 days.

(21) Appl. No.: 11/673,287

(22) Filed: Feb. 9, 2007

(65) Prior Publication Data

US 2008/0193430 A1 Aug. 14, 2008

(51) Int. Cl.
*A01N 1/02* (2006.01)
(52) U.S. Cl. .......................................................... 435/2
(58) Field of Classification Search ........................ None
See application file for complete search history.

(56) References Cited

U.S. PATENT DOCUMENTS

| | | | |
|---|---|---|---|
| 3,729,947 A | | 5/1973 | Higuchi |
| 4,389,490 A | * | 6/1983 | Crews et al. |
| 4,471,051 A | | 9/1984 | Babior et al. |
| 4,764,463 A | | 8/1988 | Mason |
| 5,378,601 A | | 1/1995 | Gepner-Puszkin |
| 5,576,213 A | | 11/1996 | Stossel |
| 5,622,867 A | | 4/1997 | Livesey |
| 5,876,676 A | | 3/1999 | Stossel et al. |
| 5,908,624 A | | 6/1999 | Scott et al. |
| 5,919,614 A | | 7/1999 | Livesey |
| 6,221,669 B1 | | 4/2001 | Livesey |
| 6,268,119 B1 | | 7/2001 | Sumita et al. |
| 6,413,713 B1 | | 7/2002 | Serebrennikov |
| 6,524,586 B2 | | 2/2003 | Scott |
| 6,555,656 B2 | | 4/2003 | Scott |
| 6,613,566 B2 | | 9/2003 | Kandler et al. |
| 6,699,465 B2 | | 3/2004 | Scott |
| 6,828,090 B2 | | 12/2004 | Lucas |
| 2002/0132225 A1 | | 9/2002 | Stossel et al. |
| 2003/0158507 A1 | | 8/2003 | Serebrennikov et al. |
| 2004/0185036 A1 | | 9/2004 | Stossel et al. |
| 2004/0223957 A1 | | 11/2004 | Lucas |
| 2005/0019743 A1 | | 1/2005 | Wagner |

FOREIGN PATENT DOCUMENTS

| | | | |
|---|---|---|---|
| EP | 0 786 934 B1 | | 5/1999 |
| EP | 1 124 413 B1 | * | 4/2003 |
| EP | 0 853 881 B1 | | 2/2004 |
| EP | 1 161 143 B1 | * | 5/2004 |
| WO | WO 94/02015 A1 | * | 2/1994 |
| WO | WO 96/13158 A2 | * | 5/1996 |
| WO | WO 97/30350 A1 | * | 8/1997 |
| WO | WO9728254 | * | 8/1997 |
| WO | WO9900145 | * | 1/1999 |
| WO | WO 00/53008 A1 | * | 9/2000 |
| WO | WO 2004/105837 A2 | * | 12/2004 |
| WO | WO 2006/044790 A2 | | 4/2006 |
| WO | WO2008027917 | * | 3/2008 |

OTHER PUBLICATIONS

Gulliksson et al., "Storage of Platelets in Additive Solutions:Effects of Phosphate", Vox Sanguinis 78 : 176-184 (2000).*
Sweeney, et al.; L-carnitine and its possible role in red cell and platelet storage; Transfusion medicine reviews (United States), Jan. 2004, 18, (1); pp. 58-65, Abstract only.*
Yasuhiko, Iwasaki; Preservation of Platelet Function on Phospholipid Polymer Surfaces; Tokyo Ika Shika Daigaku Seitai Zairyo Kogaku Kenkyujo Hokoku (Reports of the Institute of Biomaterials and Bioengineering, Tokyo Medical and Dental University), 2001, vol. 35; pp. 13-21, Abstract only.*
Murphy, Scott; The case for a new approach for documenting platelet viability; Transfusion, vol. 46, Nov. 2006 Supplement; pp. 49S-52S.
Slichter, et al.; Viability and function of 8-day-stored apheresis platelets; Transfusion, vol. 46, Oct. 2006; pp. 1763-1769.
Valeri et al.; Effect of thrombopoietin alone and a combination of cytochalasin B and ethylene glycol bis(β-aminoethyl ether) N,N'-tetraacetic acid-AM on the survival and function of autologous baboon platelets stored at 4° C for as long a 5 days [retrieved on Feb. 27, 2009] Retrieved from the Internet: <http://www.ingentaconnet.com/content/bsc/trf/2004/00000044/0000006/art00013>; 1 page.
Cold liquid-stored platelets, [retrieved on Feb. 27, 2009] Retrieved from the Internet: <http://biomed.brown.edu/Courses/BI108/BI108_2005_Groups/10/webpapges/plateletslink.htm>; 1 page.
Antigen Camouflage, [retrieved on Feb. 27, 2009] Retrieved from the Internet: <http://www.bloodbook.com/substitute.html#ANTIGEN%20CAMOUFLAGE>; 1 page.
Slichter et al.; In Vivo Studies of Autologous Platelets Stored at Room Temperature (22° C), 4° C, and 4° C with Galactosylation [retrieved on Feb. 27, 2009] Retrieved from the Internet: <http://abstracts.hematologylibrary.org/cgi/content/abstract/108/11/580?maxtoshow+&HITS+10&hits+10&RESULTFORMAT+&fulltext+Autologous+Platelets&searchid+1&FIRSTINDEX+0&sortspec+relevance&resourcetype+HWCIT>; 2 pages.
Rumjantseva et al.; Hepatocytes Ingest Longter Refrigerated Platelets: A Novel Platelet Clearance Mechanism [retrieved on Feb. 27, 2009] Retrieved from the Internet: <http://abstracts.hematologylibrary.org/cgi/content/abstract/108/11/1523?maxtoshow+&HITS+10&hits+10&RESULTFORMAT+&fulltext+%22hepatic+macrophages%22&searchid+1&FIRSTINDEX+0&volume+108&issue+11&resourcetype+HWCIT>; 1 page.
Rothwell et al.; Correlation of in vivo and in vitro functions of fresh and stored human platelets; Transfusion, vol. 40, Aug. 2000; pp. 988-993.

(Continued)

*Primary Examiner* — Sandra Saucier
(74) *Attorney, Agent, or Firm* — Schmeiser, Olsen & Watts, LLP (57) ABSTRACT

A method for storing and using platelets and an associated platelet structure. At least one modified platelet is formed. Each modified platelet includes a platelet and at least one polymerated chemical. Each polymerated chemical includes a polymer covalently bonded directly to the platelet or includes the polymer and a linker molecule such that the linker molecule is covalently bonded to the platelet and the polymer is covalently attached to the linker molecule. The polymer of each polymerated chemical of each modified platelet is polyethylene glycol (PEG) or a PEG derivative. Forming each modified platelet does not include modifying the platelet membrane of each platelet with a glycan-modifying agent. The at least one modified platelet is stored in a temperature range below 20° C. for at least one hour. After being stored, the at least one modified platelet may be introduced into a mammal.

33 Claims, 10 Drawing Sheets

OTHER PUBLICATIONS

Wandall et al.; Galactosylation does not prevent the rapid clearance of long-term 4° C stored platelets; Blood DOI 10.1182/blood-2007-06-097295 (Dec. 20, 2007); 35 pages.

Bakaltcheva et al.; Effects of Blood Product Storage Protectants on Blood Coagulation; Transfusion Medicine Reviews, vol. 17, No. 4, Oct. 2003; pp. 263-271.

Racz, Z.; Protective Effect of Cryoprotectants on Human Platelets After Repeated Freeze-Thaw Cycles; Cryo-Letters 4: 1983; pp. 193-196.

Zhang et al.; Metergasis of platelets camouflaged by mPEG with different active groups; Junshi Yixhu Kexueyuan (Bull Acad Mil Med Sci, Jun. 2007, vol. 31. No. 3; pp. 235-236.

Zhang et al.; Effect of platelet CD42a modification by mPEG-SPA with different molecular mass; Nan Fang Yi Ke Da Xue Xue Bao (J of Southern Medical University) 27(3): 2007; pp. 392-393.

Office Action (Mail Date Feb. 11, 2011) for U.S. Appl. No. 12/172,284, Filing Date Jul. 14, 2008.

* cited by examiner

COLD STORAGE OF MODIFIED PLATELETS

FIELD OF THE INVENTION

The present invention relates to method for storing and using platelets and an associated platelet structure.

BACKGROUND OF THE INVENTION

Transfusion of platelets (a commonly transfused cellular component of blood) is a cornerstone of modern medical care for a number of acute and chronic conditions characterized by either excessive bleeding or insufficiency of endogenous platelet production or function. Unlike red blood cells, which can be efficiently stored at 1-6° C. (mean 4° C.), platelets are irreversibly injured when temperatures repeatedly drop below approximately 20° C. for short periods of time or are kept at less than 20° C. for long periods of time. This injury is termed the "platelet cold storage lesion". Importantly, this platelet cold storage lesion begins to occur even after brief exposure to temperatures less than 20° C. and is even seen in patients undergoing surgery in which the temperature of the whole body or of parts of the body is decreased to temperatures less than 20° C. and leads to bleeding abnormalities.

Figure 1A:
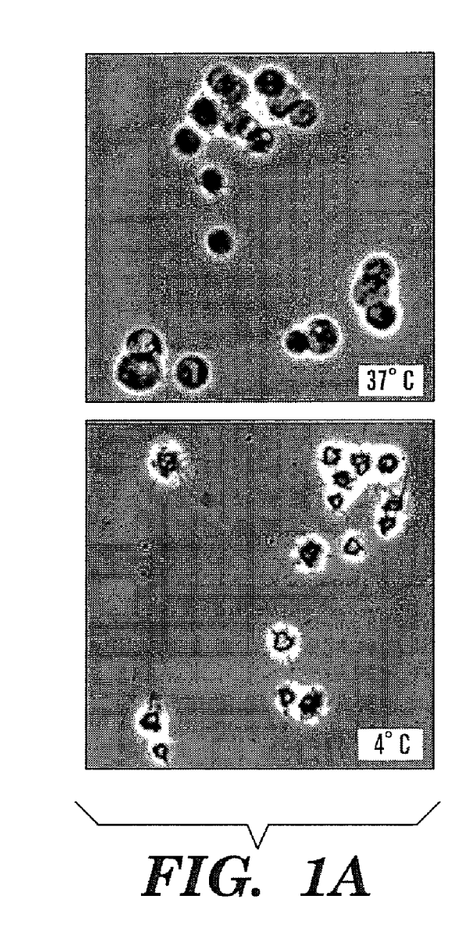
FIG. 1 depicts effects on platelets of cooling platelets from 37° C. to 4° C., in accordance with the related art.
Figure 1B:
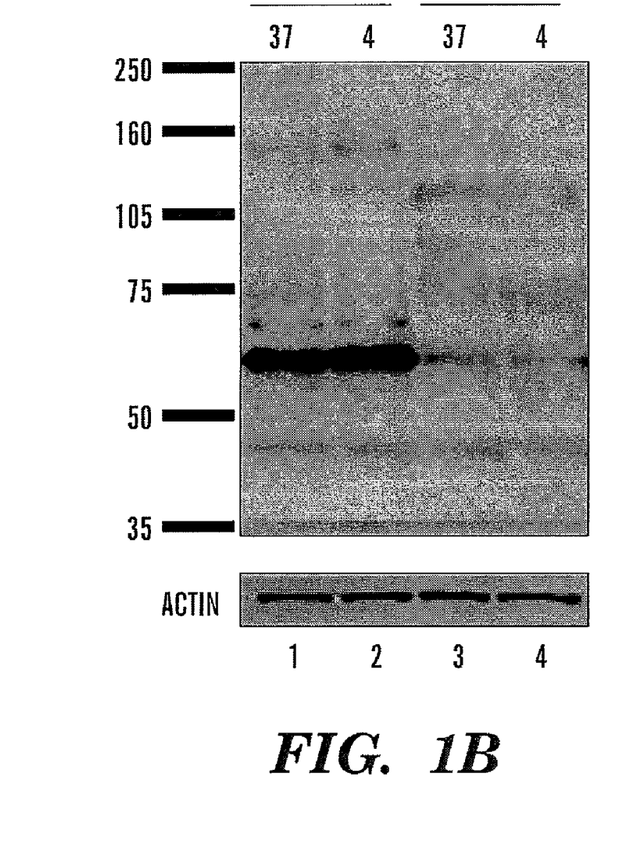

FIG. 1 depicts effects on platelets of cooling platelets from 37° C. to 4° C., in accordance with the related art. Exposure of platelets to temperatures less than 20° C. results in structural injury and functional activation of control (normal) platelets. In portion A of FIG. 1, significant morphological changes occur when platelets are cooled from 37° C. to 4° C. as shown by the appearance of filopodia using phase contrast microscopy. In portion B of FIG. 1, temperature dependent activation of platelets is further demonstrated by anti-phosphotyrosine Western Blot analysis of platelets incubated for 30 min at 37° C. (lanes 1, 3) or 4° C. (lanes 2, 4), in the absence (in lanes 1, 2) or presence (in lanes 3, 4) of a membrane-active compound. The blot was stripped and probed for actin as a loading control.

As shown in FIG. 1, key characteristics of this platelet cold storage lesion are: (1) reversible to irreversible morphological change from a discoid cell to spiculated spheres with protruding filopodia, depending on time at temperatures less than 20° C.; (2) irreversible immune-independent microaggregation of platelets (i.e., increased cell: cell interaction); (3) membrane clustering of the glycoprotein GPIb on the surface of platelets resulting in the formation of a neoantigen; and (4) subsequent recognition and phagocytosis by macrophages of the microaggregates and/or neoantigen-expressing platelets upon transfusion into a recipient. In addition, there is a significant reduction in circulation half-life of chilled platelets introduced into a recipient of the chilled platelets. As a consequence of this platelet cold storage lesion, platelets must be stored at 20-24° C. (mean of 22° C.) in order to maintain acceptable function and viability in the transfused patient (see American Association of Blood Banks (AABB) Technical Manual). Unfortunately, maintaining platelets at a mean temperature of 22° C. for prolonged periods of time greatly increases the risk of adverse medical events due to bacterial growth in the platelet product. Current estimates are that 1 in every 3000 platelet units are affected by microbial contamination (see Kleinman S H et al., "Two-year experience with aerobic culturing of apheresis and whole blood-derived platelets", Transfusion 2006, 46:1787-1794). Risks are associated with transfusion of cellular blood components in Canada (see Transfusion Medicine Reviews, 17:120-163). Because of this microbial risk, platelets can only be stored at 20-24° C. for a maximum of 5 days before they must be destroyed.

Rosiello (International Publication No. WO 2006/044790 A2) discloses a method for the cold storage (−80° C. to 15° C.) of platelets for periods of 3 days to 28 days, by modifying the platelet membrane with a glycan-modifying agent, namely a sugar, a monosaccharide sugar, a nucleotide sugar, sialic acid, sialic acid precursors, CMP-sialic acid, UDP-galactose, and UDP-galactose precursors. Rosiello's method is not practical, however, because it is known that glycosylation (i.e., binding saccharides to proteins and/or lipids) fails to restore the functionality of chilled platelets in vivo.

For example, the inventors of the present invention were present at a seminar at the Center for Blood Research at the University of British Columbia on Apr. 26, 2006 at which Dr. Karin Hoffmeister gave a public presentation entitled "Platelet Glycosylation and the "In and Outs" of Platelet Transfusion"during which Dr. Hoffmeister talked about the problems that had been encountered with glycosylation, said problems including the fact that glycosylation does not protect platelets in chilled platelet concentrates.

In addition, Hans Wandall of Zymequest, Inc. gave a public presentation in California at the annual meeting of the California Blood Bank Society on Apr. 28, 2006 in which Hans Wandall substantiated that "glycosylation of platelets does not work, at least after extended storage in the cold and not for larger volumes," which was confirmed by an attendee of said public presentation by Hans Wandall to an inventor of the present invention via email correspondence on Jun. 22, 2006.

In addition, at a meeting of the American Society of Hematology on Dec. 11, 2006, S. J. Schlichter et al. reported the result of studies relating to galactosylated platelets derived from humans and stored a 4° C. and concluded: "The data show that, following two days of 4° C. storage, the recoveries and survivals of the galactosylated platelets are no different than the non-galactosylated 4° C. stored platelets from the same volunteer. Although the recoveries of the 4° C. stored platelets with and without galactosylation are well-maintained compared to the 22° C. stored platelets, the survivals are markedly reduced as had been previously shown for 4° C. stored platelets (Br J Haematol 1976; 34:403)." (see S. J. Schlichter et al., Abstract HEMO6L1__379: Contract View, American Society of Hematology, Dec. 9, 2006, http://127.0.0.1:9080/HEMO6/view.y?nu=HEMO6L1__ 379&terms=580).

Thus, there is a need for a method for storing platelets for more than five days such that the stored platelets have acceptable platelet functionality and viability after being introduced into a patient.

SUMMARY OF THE INVENTION

The present invention provides a method for storing platelets, comprising:

forming at least one modified platelet, each modified platelet comprising a platelet and at least one polymerated chemical, each polymerated chemical either comprising a polymer covalently bonded directly to the platelet membrane of the platelet or comprising the polymer and a linker molecule such that the linker molecule is covalently bonded to the platelet membrane of the platelet and the polymer is covalently attached to the linker molecule, the polymer of each polymerated chemical of each modified platelet being independently selected from the group consisting of polyethylene glycol (PEG) and a PEG derivative, said forming the at least one platelet not comprising modifying the platelet membrane of each platelet with a glycan-modifying agent; and storing the at least one modified platelet in a temperature range below 20° C. for a time period of at least one hour.

The present invention provides a method for using platelets, comprising:

introducing at least one modified platelet into a mammal after the at least one platelet had been stored in a temperature range below 20° C. for a time period of at least one hour, each modified platelet comprising a platelet and at least one polymerated chemical, each polymerated chemical either comprising a polymer covalently bonded directly to the platelet membrane of the platelet or comprising the polymer and a linker molecule such that the linker molecule is covalently bonded to the platelet membrane of the platelet and the polymer is covalently attached to the linker molecule, the polymer of each polymerated chemical of each modified platelet being independently selected from the group consisting of polyethylene glycol (PEG) and a PEG derivative, said at least one modified platelet not comprising a modification of the platelet membrane of each platelet with a glycan-modifying agent.

The present invention provides a platelet structure, comprising:

at least one modified platelet at a temperature below 20° C., each modified platelet comprising a platelet and at least one polymerated chemical, each polymerated chemical either comprising a polymer covalently bonded directly to the platelet membrane of the platelet or comprising the polymer and a linker molecule such that the linker molecule is covalently bonded to the platelet membrane of the platelet and the polymer is covalently attached to the linker molecule, the polymer of each polymerated chemical of each modified platelet being independently selected from the group consisting of polyethylene glycol (PEG) and a PEG derivative, said at least one modified platelet not comprising a modification of the platelet membrane of each platelet with a glycan-modifying agent.

The present invention provides a method for storing platelets for more than five days such that the stored platelets have acceptable platelet functionality and viability after being introduced into a patient.

DETAILED DESCRIPTION OF THE INVENTION

The present invention provides a method, system, and structure for safely storing modified platelets at temperatures of less than 20° C. subsequent to formation of the modified platelets. The modified platelets are formed by covalent modification of the platelet membrane of the platelets with polyethylene glycol ("PEG") or derivatives of poly(ethylene glycol) such as methoxypolyethylene glycol ("mPEG"). The covalent modification of the platelets with PEG or a PEG-derivative blocks the adverse effects of the platelet cold storage lesion while maintaining acceptable platelet function and viability (e.g., normal platelet function and viability). Normal in vitro platelet functionality is defined as full aggregation of platelets in plasma in response to 2 IU/mL thrombin (75-100% increase in light transmission measured by platelet aggregometry test, as illustrated in portion 72 of FIG. 8, described infra) and the potential to recover from mild stress, i.e., recover resting morphology after mild temperature or osmotic stress. Normal in vivo functionality is defined as 67 percent mean post-transfusion recovery of resting morphology (range 50-80%) of stored platelets compared to fresh platelets and 50 percent mean post-transfusion survival (range 30-70%) of stored platelets compared to fresh platelets measured 1 hour or 24 hours after transfusion with both fresh and stored platelets being obtained from the same human being or mammal (Slichter S J et al 2006 "Viability and function of 8-day-stored apheresis platelets", *Transfusion*. 46 1763-9; and Murphy S. 2006 "The case for a new approach for documenting platelet viability", *Transfusion*. 46 Suppl. 49S-51S).

With the present invention, modified platelets can be stored for prolonged periods of time (e.g., more than 5 days) at temperatures less than 20° C. (e.g., 4° C.) which significantly inhibits bacterial growth during the cold storage of the platelets. This invention is applicable in the traditional blood banking environment as well as in specific medical interventions involving the transient cooling of the whole or partial body to a temperature of less than 22° C. Thus, the present invention satisfies a long-felt, previously unsatisfied need in transfusion medicine for storing platelets under cooling temperature conditions that inhibit microbial growth while maintaining acceptable platelet function and viability.

Figure 2:
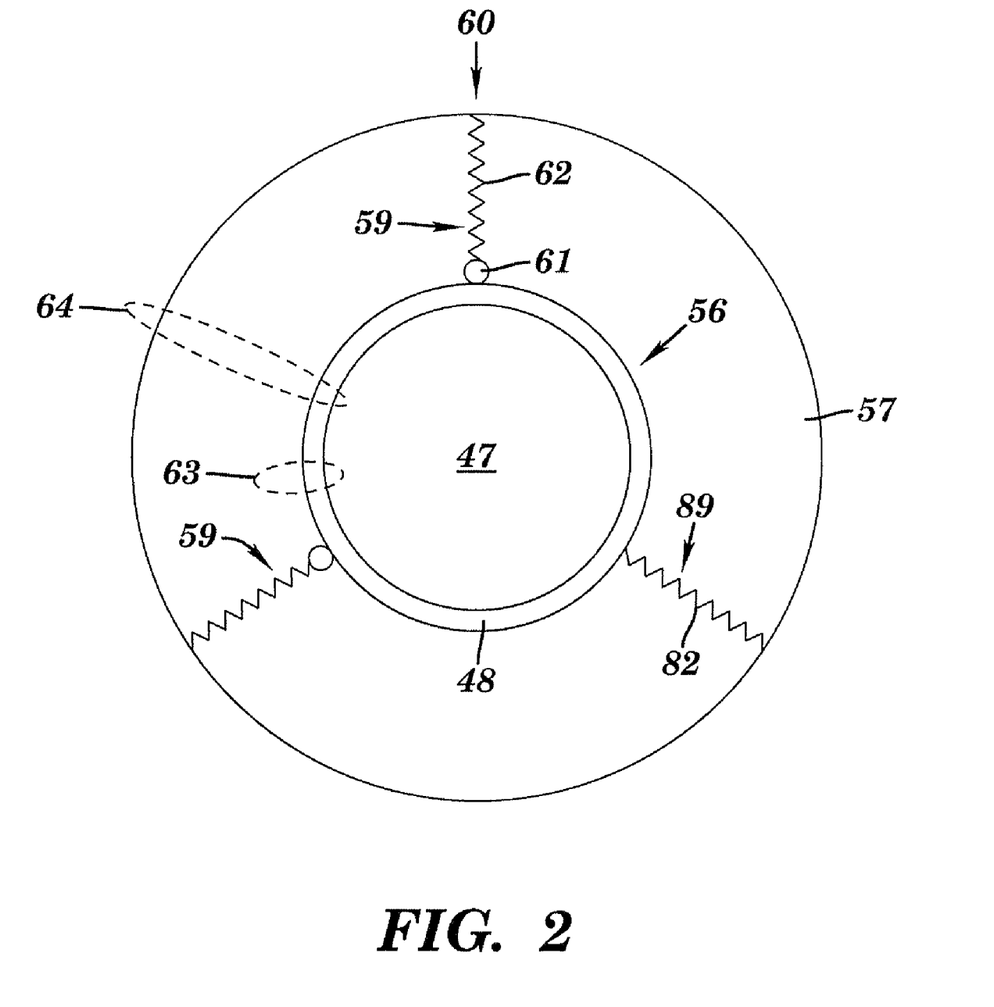
FIG. 2 is a schematic representation of a modified platelet, in accordance with embodiments of the present invention.

FIG. 2 is a schematic representation of a modified platelet 60, in accordance with embodiments of the present invention. The modified platelet 60 comprises a platelet 56 and at least one polymerated chemical 59. In one embodiment, the at least one polymerated chemical 59 consists of a plurality of polymerated chemicals 59. The platelet 56 includes a platelet core 47 and a platelet membrane 48 that surrounds the platelet core 47. Each polymerated chemical 59 is covalently bonded to the platelet membrane 48 of the platelet 56. More specifically in one embodiment, each polymerated chemical 59 comprises a linker molecule 61 and a polymer 62, wherein the polymer 62 is covalently attached to the linker molecule 61 and the linker molecule 61 is covalently bonded to the platelet membrane 48 at a bonding site (e.g., at a protein or at a carbohydrate) of the platelet membrane 48. The linker molecule serves to activate the covalent linkage of the polymer 62 to the platelet 56 at the platelet membrane 48.

In an alternative embodiment, a polymerated chemical 89 comprises a polymer 82 covalently bonded directly to the platelet membrane 48 at a bonding site (e.g., at a protein or at a carbohydrate) of the platelet membrane 48. The polymerated chemical 89 is analogous to the polymerated chemical 59, except that the polymerated chemical 89 does not comprise a linker molecule 61, and the polymer 82 is analogous to the polymer 62. Although the discussion infra describes the present invention for the embodiment of the polymerated chemical 59 that comprises the linker molecule 61 and the polymer 62, it should be understood that unless otherwise indicated or otherwise inapplicable, said discussion infra applies likewise to the alternative embodiment of the polymerated chemical 89 that comprises the polymer 82, wherein the polymer 82 is covalently bonded directly to the platelet membrane 48.

The space defined by the at least one polymerated chemical 59 is an envelope 57 that envelopes the platelet 56 due to a "long chain length" of each polymer 62 (i.e., a chain length that is sufficient magnitude to fill the space around itself). The envelope 57 provides a immunocamouflage functionality. A small membrane protein 63 (such as CD9=p24) is covered by the envelope 57 and cannot bind its respective antibody. A large, extended membrane protein 64 (such as CD42b=GPIb) is partially covered by the envelope 57 and reaches through the envelope 57, and can still be recognized and bound by the respective antibody as well as other proteins important for the hemostatic function of platelets. The envelope 57 prevents the formation and/or immunologic recognition of GPIb-clusters and microaggregation.

The polymer 62 in each polymerated chemical 59 is independently selected from the group consisting of polyethylene glycol (PEG) and a PEG derivative. Polyethylene glycol has the formula $H(OCH_2CH_2)_nOH$, wherein n is greater than or equal to 4, with a molecular weight of up to about 20,000 Daltons. Various derivatives of polyethylene glycol may substitute for the H or OH end groups, forming, for example, polyethylene glycol ethers (e.g., PEG-O—R; PEG-O—$CH_3$; $CH_3$-PEG-OH); 2,4-dinitrophenyl ethers of PEG), polyethylene glycol esters (e.g., PEG-$O_2C(CH_2)_{14}CH_3$; PEG-$O_2CCH_2CH_2CO_2$-atropine), polyethylene glycol amides (e.g., PEG-$O_2C(CH_2)_7CONHR$; mPEG-$O_2CCH_2CH_2CONH(CH_3)CHCH_2C_6H_5$; PEG-$O_2CCH_2CH_2CONHCH_2CH_2$-$NAD^+$), polyethylene glycol amines (e.g., PEG-$NH_2$; PEG-$NH(CH_2)_6NH_2$; PEG-$OCH_2CH_2NH_2$; mPEG-$NH_2$), polyethylene glycol acids (e.g., PEG-$O_2C(CH_2)_2CO_2H$; PEG-O-$CH_2CO_2H$; PEG-$O_2C$—$(CH_2)_7$—$CO_2H$), polyethylene glycol aldehydes (e.g., PEG-O—$CH_2$—CHO), and electrophilic derivatives (e.g., PEG-Br; PEG-$OSO_2CH_3$; PEG-O). Various phenyl moieties can also be substituted for the H or OH of PEG, such as the 2,4-dinitrophenyl ether of PEG mentioned above. The particular polyethylene glycol derivatives listed above are exemplary only, and the invention is not intended to be limited to those particular examples.

The linker molecule 61 may comprise, inter alia, cyanuric chloride, imidazolyl formate, succinimidyl succinate, succinimidyl carbonate, succinimidyl glutarate, N-hydroxysuccinimide, 4-nitrophenol, and 2,4,5-trichlorophenol. The linker molecules listed above are exemplary only, and the invention is not intended to be limited to those particular examples. Any linker molecule capable of covalently attaching to the polymer 62 and mediating the linkage of the polymer to the platelet membrane 48 may be similarly used.

Figure 3:
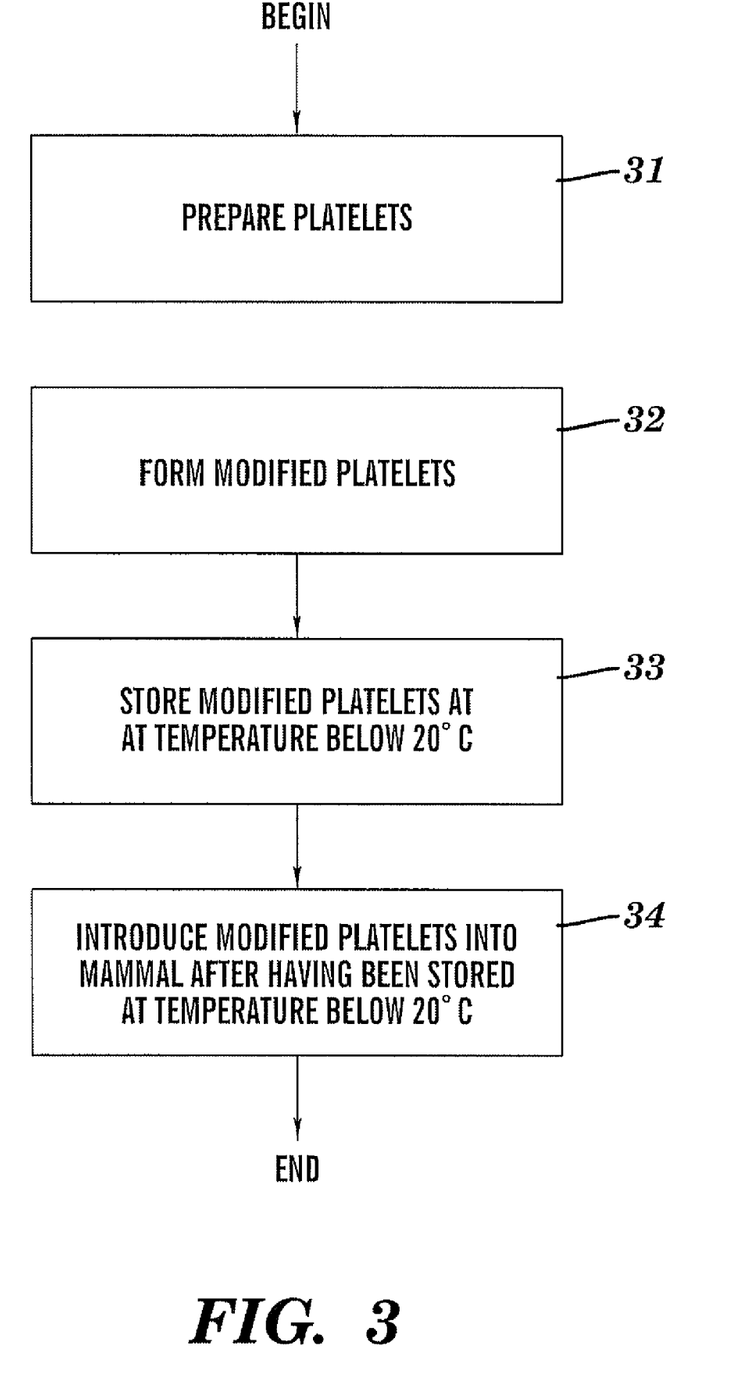
FIG. 3 is a flow chart of a method of forming and using modified platelets, in accordance with embodiments of the present invention.

FIG. 3 is a flow chart of a method of forming and using modified platelets, in accordance with embodiments of the present invention. The flow chart of FIG. 3 comprises steps 31-34.

Step 31 prepares at least one platelet (e.g., a plurality of platelets), using any known platelet preparation method such as, inter alia, whole blood-derived platelet rich plasma (PRP) platelets, whole blood-derived buffy coat platelets, or apheresis platelets.

Step 32 forms at least one modified platelet from the at least one platelet prepared in step 31. Each modified platelet conforms to the modified platelet 60 of FIG. 2 and comprises a platelet and at least one polymerated chemical. Each polymerated chemical either comprises a polymer covalently bonded directly to the platelet membrane of the platelet or comprises the polymer and a linker molecule such that the linker molecule is covalently bonded to the platelet membrane of the platelet and the polymer is covalently attached to the linker molecule. The polymer of each polymerated chemical of each modified platelet is independently selected from the group consisting of polyethylene glycol (PEG) and a PEG derivative. Step 32 does not comprise modifying the platelet membrane of the platelets with a glycan-modifying agent, because it is known that glycosylation (i.e., binding saccharides to proteins and/or lipids) fails to preserve the functionality of chilled platelets in vivo as indicated supra. Indeed, it is totally outside of the scope of the present invention to modify the platelet membrane of the platelets with a glycan-modifying agent.

In one embodiment, a polymer of a polymerated chemical of a modified platelet of the at least one modified platelets consists of PEG. For example, the modified platelet 60 of FIG. 2 comprises at least one polymerated chemical, and the polymer of one polymerated chemical of the at least one polymerated chemical may consist of PEG.

In one embodiment, a polymer of a polymerated chemical of a modified platelet of the at least one modified platelet consists of a PEG derivative. For example, the modified platelet 60 of FIG. 2 comprises at least one polymerated chemical, and the polymer of one polymerated chemical of the at least one polymerated chemical may consist of a PEG derivative.

In one embodiment, a polymer of a polymerated chemical of a first modified platelet of the at least one modified platelet consists of a first PEG derivative, and a polymer of a polymerated chemical of either the first modified platelet or a second modified platelet of the at least one modified platelet consists of a second PEG derivative that differs from the first PEG derivative. The preceding embodiment is describing cases in which two different PEG derivatives (e.g., PEG-O—$CH_3$ and $CH_3$-PEG-OH) are present in a plurality of modified platelets, wherein the plurality of modified platelets comprise a first modified platelet and a second modified platelet. These two different PEG derivatives are denoted as a first PEG derivative and a second PEG derivative. In one case, both the first PEG derivative and the second PEG derivative are in the first modified platelet. In another case, the first PEG derivatives is in the first modified platelet and the second PEG derivative is in the second modified platelet.

Step 33 stores the modified platelets formed in step 32 in a temperature range below 20° C. for a time period of at least one hour. In one embodiment, the modified platelets are stored in a platelet additive solution. In one embodiment, the temperature range below 20° C. is a single temperature characterized by an approximately constant value of temperature (e.g., 0° C., 4° C., 10° C., etc.). In one embodiment, the temperature range below 20° C. is, inter alia: from −50° C. to below 20° C., from 0° C. to below 20° C., from 4° C. to 14° C., etc. The time period of at least one hour may, inter alia: be in a range from 1 day to five days, exceed 5 days, be in a range from more than 5 days to 30 days, be in a range from 30 days to 3 months, exceed 3 months, be in a range from 3 months to 1 year, etc.

The storage of the modified platelets in the temperature range below 20° C. for the time period of at least one hour in step 33 prevents and/or retards microbial growth on the stored platelets during the time period.

In one embodiment, the platelets prepared in step 31 were obtained from an animal (i.e., a mammal) and after the storing step 33 has been performed, the modified platelets have a post-transfusion resting morphology recovery in the animal of 50% to 80%, relative to fresh platelets from the animal, at a post-transfusion time in a range of 1 hour to 24 hours measured from a time of transfusion of the modified platelets and the fresh platelets into the animal. This means that if the post-stored platelets were transfused into the animal, then the percentage of the transfused post-stored platelets that would recover its resting morphology is 50% to 80% of the percentage of fresh platelets that would recover its resting morphology, at a post-transfusion time in a range of 1 hour to 24 hours measured from a time of the transfusion of the post-stored platelets and the fresh platelets into the animal. In this embodiment, the animal may be the same mammal into which the modified platelets are introduced in step 34 (described infra) or the animal may be another mammal. The modified platelets consist of at least N modified platelets, N being a minimum number of modified platelets necessary for a determination of the post-transfusion resting morphology recovery to have a statistical error not exceeding a specified threshold percent. The specified threshold percent may be in a range of 1% to 20% or any subset thereof (e.g., 5%, 10%, 5 to 15%, 10% to 20%, 20%, etc.). In this embodiment, the post-transfusion resting morphology recovery is an acceptable post-transfusion resting morphology recovery.

In one embodiment, the platelets prepared in step 31 were obtained from an animal (i.e., a mammal) and after the storing step 33 has been performed, the modified platelets have a post-transfusion survival in the animal of 30% to 70%, relative to fresh platelets from the animal, at a post-transfusion time in a range of 1 hour to 24 hours measured from a time of transfusion of the modified platelets and the fresh platelets into the animal. This means that if the post-stored platelets were transfused into the animal, then the percentage of the transfused post-stored platelets that would survive is 30% to 70% of the percentage of fresh platelets that would survive, at a post-transfusion time in a range of 1 hour to 24 hours measured from a time of the transfusion of the post-stored platelets and the fresh platelets into the animal. In this embodiment, the animal may be the same mammal into which the modified platelets are introduced in step 34 (described infra) or the animal may be another mammal. The modified platelets consist of at least N modified platelets, N being a minimum number of modified platelets necessary for a determination of the post-transfusion survival to have a statistical error not exceeding a specified threshold percent. The specified threshold percent may be in a range of 1% to 20% or any subset thereof (e.g., 5%, 10%, 5 to 15%, 10% to 20%, 20%, etc.). In this embodiment, the post-transfusion survival is an acceptable post-transfusion survival.

Step 34 introduces the modified platelets into a mammal after having been stored at temperature below 20° C. for the time period in step 33. In one embodiment, the mammal is a human being. In one embodiment, the mammal is a non-human mammal (e.g., dog, cat, horse, rat, etc.).

The modified platelets introduced into the mammal in step 34 have a longer circulation half-life in the mammal than would a same number of non-modified platelets introduced into the mammal after being stored in the temperature range below 20° C. for the time period. The non-modified platelets would be processed in accordance with the flow chart of FIG. 3 except that step 32 is not performed. Thus, the non-modified platelets are prepared as in step 31, stored at temperature below 20° C. for the time period of at least one hour as in step 33, and introduced into the animal as in step 34.

Figure 4:
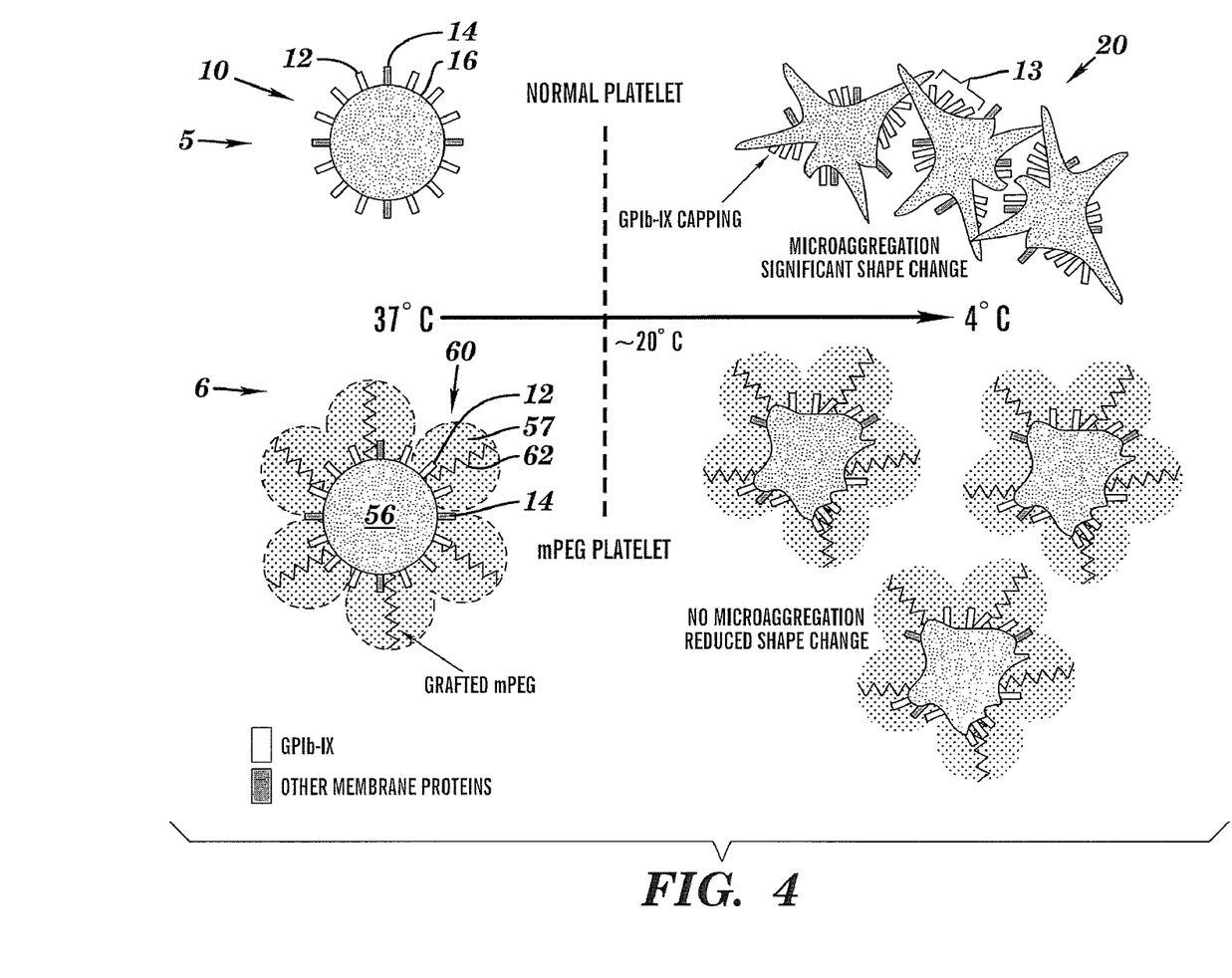
FIG. 4 contrasts mPEG grafted platelets with normal platelets with respect to the respective platelets being chilled, in accordance with embodiments of the present invention.

FIG. 4 contrasts mPEG grafted platelets with normal platelets with respect to the respective platelets being cooled, in accordance with embodiments of the present invention.

In the upper portion 5 of FIG. 4, normal platelets 10 comprise glycoprotein (GP) Ib 12 and other membrane proteins 14 inherent to the platelet membrane 16. The normal platelets 10, upon being cooled from 37° C. to 4° C., aggregate with significant shape change wherein the GP Ib 12 form GP Ib clusters 13 at the platelet membrane 16 outer surface in the transformation of the normal platelets 10 to the cooled platelets 20. After introduction of the cooled platelets 20 into a subject, the GP1b clusters 13 are recognized by CR3 receptors of liver macrophages, which leads to the phagocytosis of the previously cooled platelets 20.

In the lower portion 6 of FIG. 4, the polymerated chemical 59 of FIG. 2 surrounds the platelet 56 to form the modified platelet 60, which is cooled from 37° C. to 4° C., wherein the envelope 57 provides a immunocamouflage functionality that prevents microaggregation of the platelets and reduces platelet shape change upon said cooling. Furthermore, the formation and/or immunologic recognition of GPIb-clusters 13 and other membrane proteins is attenuated due to the envelope 57.

Figure 5:
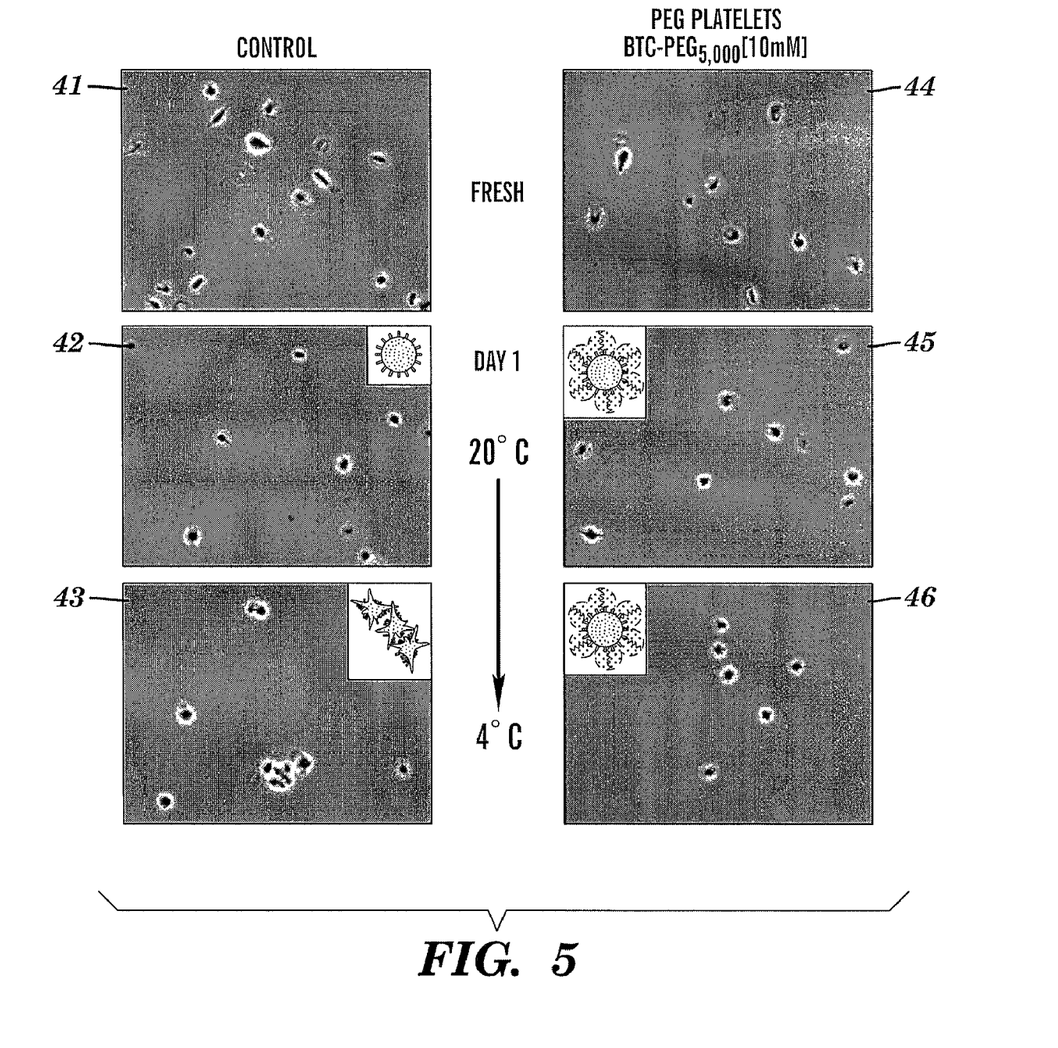
FIG. 5 depicts modification of platelets with 10 mM BTC-PEG (5000 kDa), in accordance with embodiments of the present invention.

FIG. 5 depicts modification of platelets with 10 mM BTC-PEG (5000 kDa), in accordance with embodiments of the present invention. FIG. 5 comprises normal platelets acting as a control in panels 41-43 and PEG-modified in panels 44-46. Panels 41 and 44 depict the normal and modified platelets, respectively, as fresh platelets or platelets following 24 fours of storage at or above 20° C. Panels 42 and 45 depict the normal and modified platelets, respectively, at 20° C. Panels 43 and 46 depict the normal and modified platelets, respectively, at 4° C.

As seen in panels 41-42 and 44-45, the platelet modification of the modified platelets does not change platelet morphology of fresh platelets or following 24 hours storage at or above 20° C. Furthermore, PEGylation of platelets prevents platelet activation and microaggregation at 4° C., as shown for the modified platelets in panel 46 in comparison with the control platelets in panel 43.

Figure 6:
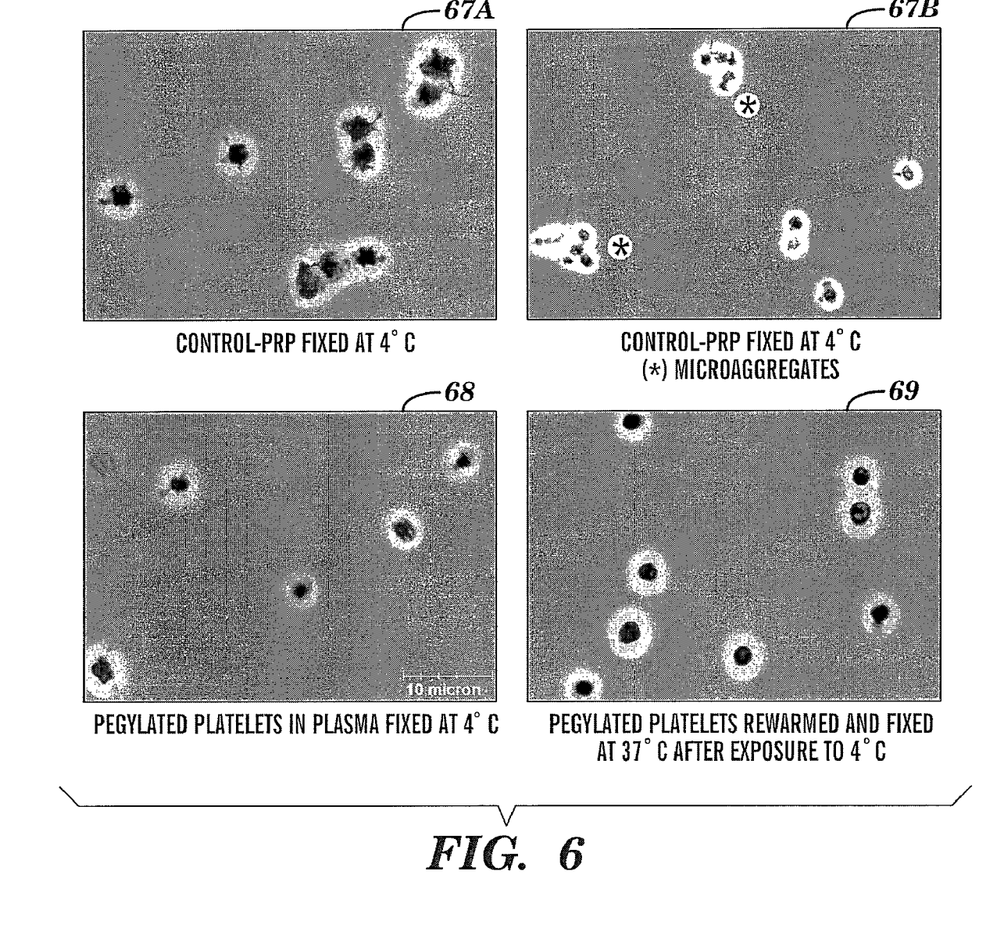
FIG. 6 depicts the effect on morphological changes and microaggregation of cooling and subsequent rewarming of PEG-modified platelets, in accordance with embodiments of the present invention.

FIG. 6 depicts the effect on morphological changes and microaggregation of cooling and subsequent rewarming of PEG-modified platelets, in accordance with embodiments of the present invention. FIG. 6 comprises panels 67A, 67B, 68, and 69. Panel 67A depicts normal control platelets from platelet concentrates or platelet rich plasma (PRP) fixed at 4° C. Panel 67B depicts microaggregation of normal control platelets from platelet concentrates or platelet rich plasma (PRP) fixed at 4° C. Panel 68 depicts PEGylated platelets in plasma fixed at 4° C. Panel 69 depicts PEGylated platelets rewarmed and fixed at 37° C. after exposure to 4° C. FIG. 6 shows that PEGylation of platelets prevents both significant morphological changes and microaggregation of platelets at or after 30 minutes at 4° C. Furthermore, PEGylated platelets regain normal morphology upon rewarming to 37° C.

As seen in panel 67, the normal control platelets from platelet concentrates or PRP undergo severe morphological changes and form small aggregates when exposed to low temperature (4° C.). Phase contrast microscopy shows long pseudopods and platelet-platelet interactions. As seen in panel 68, PEGylation inhibits severe morphological changes as well as platelet interactions at 4° C. As seen in panel 69, a smooth, resting morphology was restored by incubation at 37° C., which indicates that upon rewarming from 4° C. to 37° C., PEGylated platelets are viable and minor morphological changes caused by chilling are reversible.

Figure 7:
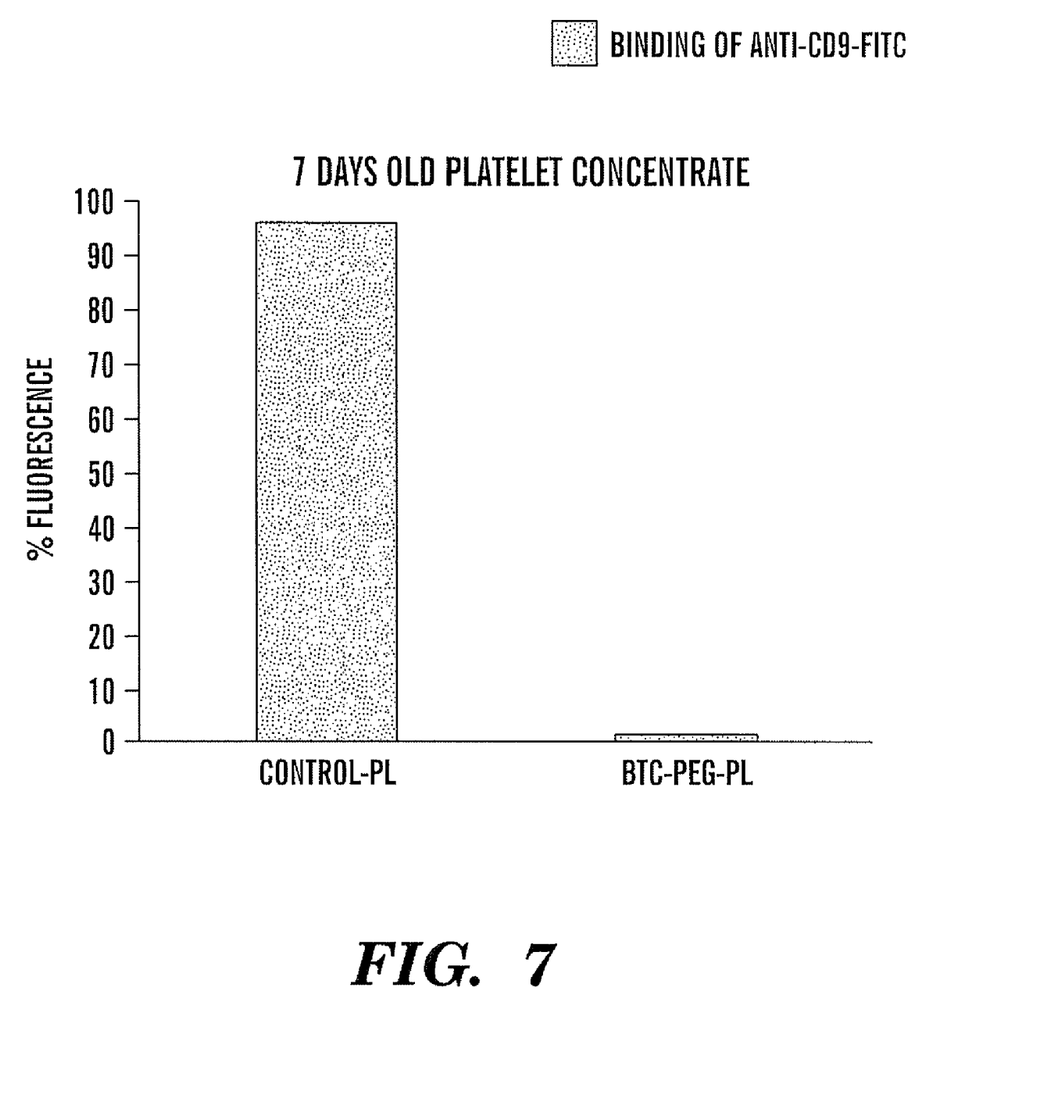
FIG. 7 depicts PEGylation of 7 day old platelet concentrates, in accordance with embodiments of the present invention.

FIG. 7 depicts PEGylation of 7 day old platelet concentrates, in accordance with embodiments of the present invention. PEGylation of 7 day old platelet concentrates prevents recognition of platelet surface (e.g., CD9) and activation (e.g., CD62) markers. Shown is anti-CD9 binding to 7 day old platelets (washed before and after reaction with 0 or 10 mM BTC-PEG$_{5000}$). CD9 antigens were effectively masked on washed PEGylated platelets, which was shown as complete inhibition of FITC-labeled anti-CD9 binding to these platelets. In contrast, control platelets demonstrated ~100% anti-CD9 binding and therefore ~100% of platelets have fluorescently (FITC) labeled antibody bound to them. In FIG. 7 the extent of FITC labeling is shown as % Fluorescence.

Figure 8:
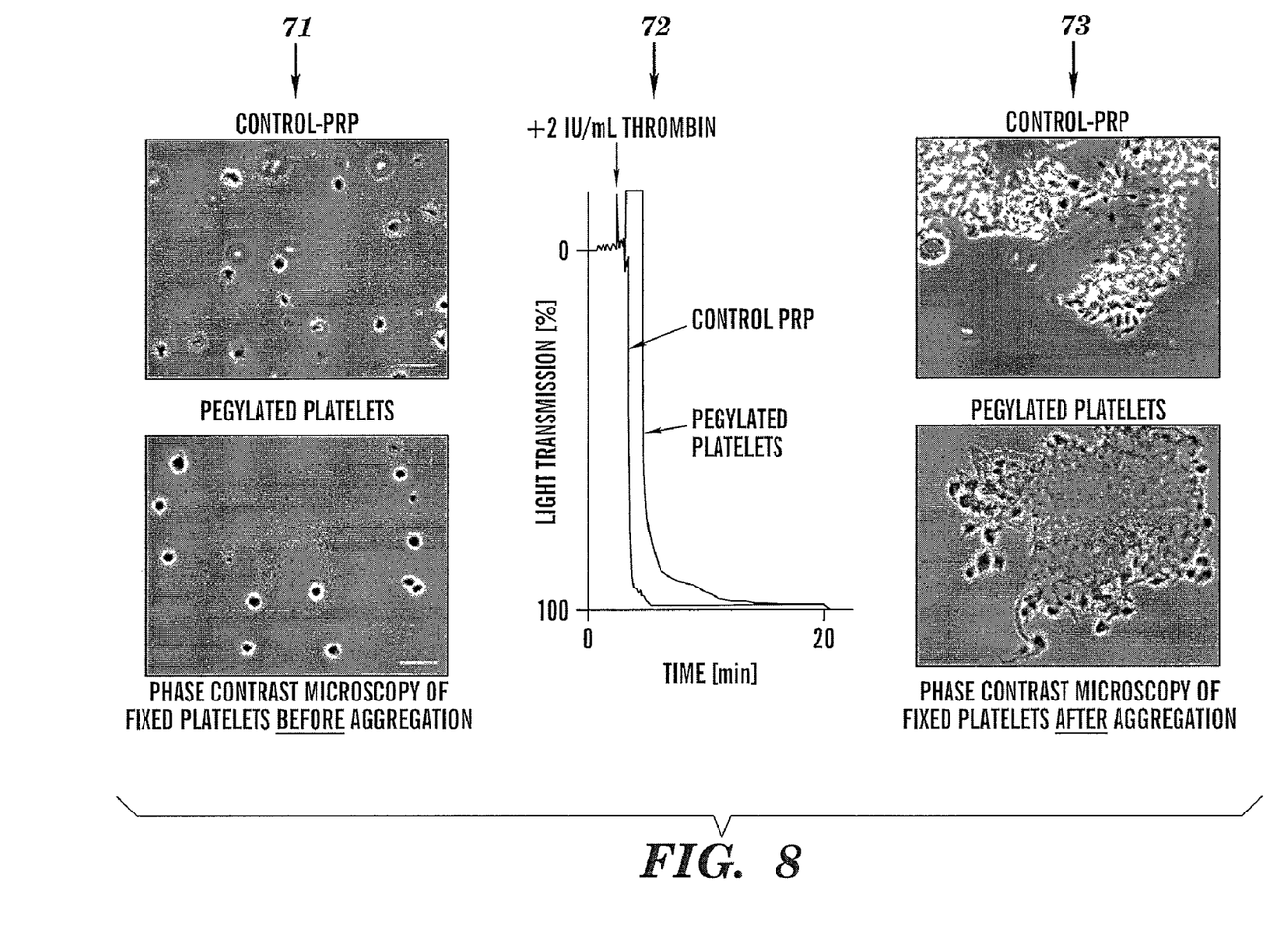
FIG. 8 depicts the response of PEGylated platelets to platelet agonists, in accordance with embodiments of the present invention.

FIG. 8 depicts the response of PEGylated platelets to platelet agonists, in accordance with embodiments of the present invention. FIG. 8 shows that PEGylated platelets are fully functional and aggregate in vitro in response to platelet agonists (e.g., thrombin). In portion 71 of FIG. 8, phase contrast microscopy of control platelets in plasma and PEGylated platelets in plasma shows that PEGylated platelets maintain a smooth, resting morphology. In portion 72 of FIG. 8, in response to 2 IU/mL thrombin, control platelets and PEGylated platelets fully aggregate at 37° C. with 1000 rpm stir speed in the aggregometer (ChronoLog). In portion 73 of FIG. 8, control and PEGylated platelets form microscopically very similar thrombin-induced clots demonstrating normal biological function. Aggregates depicted in portion 73 of FIG. 8 came from samples fixed at the end of the experiment shown in portion 72.

Figure 9A:
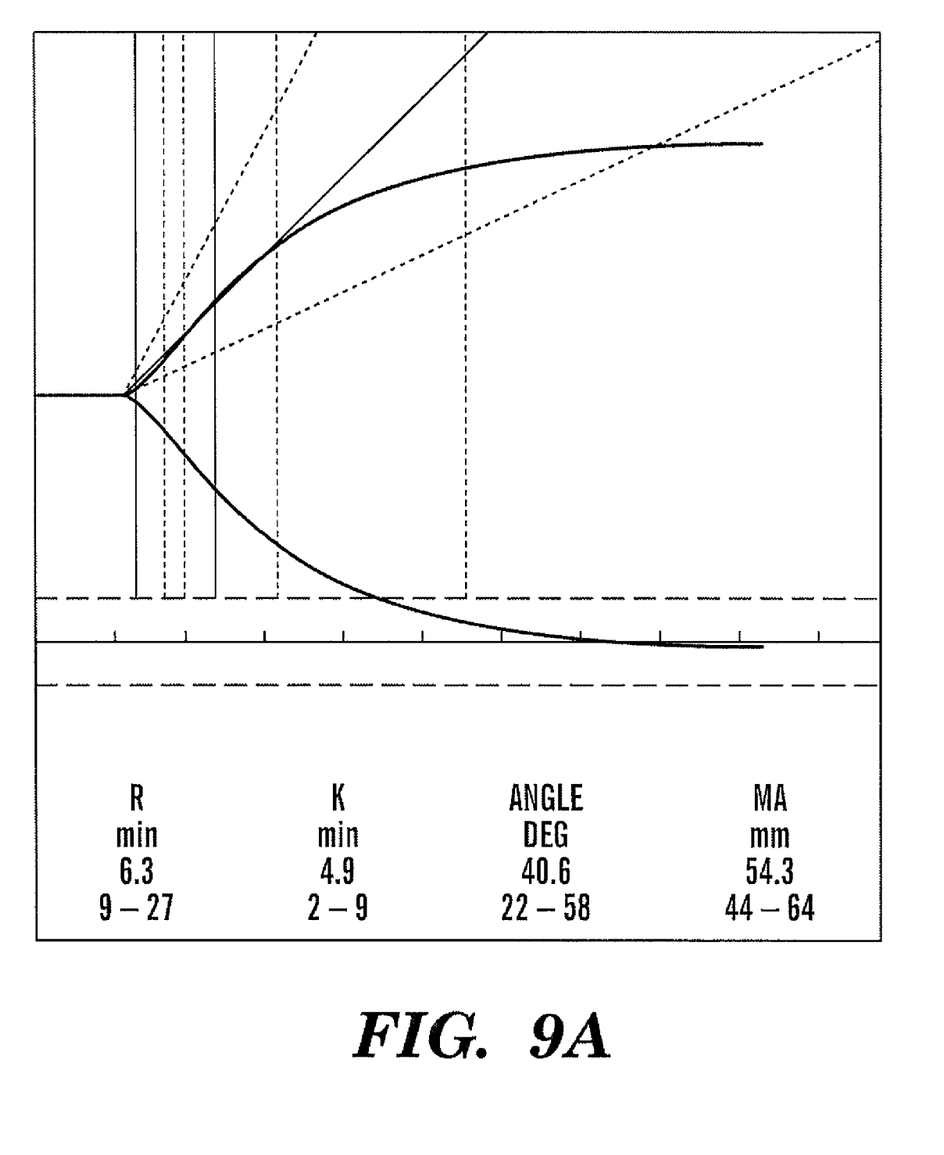
FIGS. 9A and 9B depict thromboelastography (TEG) of PEGylated platelets, in accordance with embodiments of the present invention.
Figure 9B:
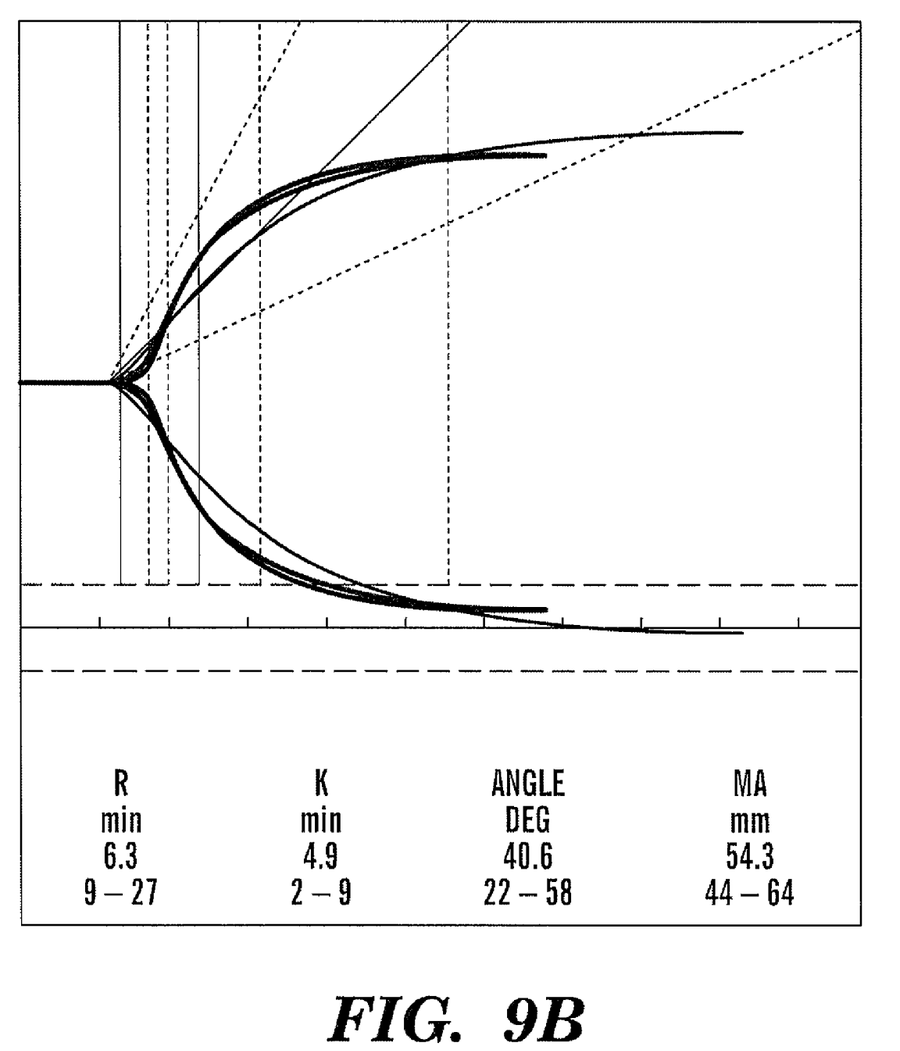

FIGS. 9A and 9B depicts thromboelastography (TEG) of PEGylated platelets, in accordance with embodiments of the present invention. The TEG in FIGS. 9A and 9B demonstrates normal platelet function for the PEGylated platelets.

In FIG. 9A, platelet mapping with TEG determines total platelet function. The two symmetric arms show the same results. The parameter definitions are: R: time required for initial fibrin formation); Kc: time to reach a certain level of clot strength (clot kinetics); Angle: speed of fibrin build-up and cross-link (clot strengthening); MA: maximum amplitude: dynamic properties of fibrin and platelet bonding through GPIIb-IIIa.

In FIG. 9B, representative findings obtained with acid citrate dextrose (ACD) anticoagulated control platelets and PEGylated platelets are overlaid on the generic tracing expected for normal whole blood. Both control and PEGylated platelet products fall within the expected ranges; i.e., the speed of fibrin formation and build-up is equivalent and the dynamic properties of fibrin as well as platelet bonding through GPIIb-IIIa/fibrinogen are the same for control and PEGylated platelets.

The following methodology describes an example of how the modified platelets of the present invention may be formed.

Platelet modification with PEG or PEG derivatives is done by mixing a concentration of platelets with chemically activated PEG or PEG derivatives. The concentration of platelets can range from very low counts to very high counts as required by the application; for clinical purposes, a single unit of platelet rich plasma (PRP) should contain at least $5.5 \times 10^{10}$ platelets (see AABB Technical Manual, $12^{th}$ edition, 1996 American Association of Blood Banks, page 144). Activation of PEG or PEG derivatives is accomplished by chemically modifying one or both terminal reactive groups of PEG or PEG derivatives with a chemical reactive linker group of an associated linker molecule.

Multiple mixing methods can be used to achieve the desired platelet-PEG ratio. In one embodiment, whole blood is collected in ACD (acid citrate dextrose) anticoagulant. Platelet rich plasma (PRP) is prepared from the whole blood by centrifugation (150×g for 12 minutes). Platelet numbers are determined using an automated cell counter. The PRP is mixed with the desired concentration of activated PEG or PEG-derivative using an automated mixing instrument so as to achieve a uniform platelet-PEG ratio. The platelet-PEG mixture is collected and allowed to react for 30 minutes at room temperature. Both the reaction time and temperature can be varied. For example, the reaction time could range from 1 minute to greater than 60 minutes. The reaction time is governed in part by the reactivity of the linker molecule as well as the desired efficiency of the reaction. The temperature should be greater than 20° C. to avoid cold induced injury prior to the protection afforded by the grafted PEG or PEG-derivative.

Following derivatization, the modified platelets can be used as is, or can undergo gentle washing and centrifugation in physiologic solutions (e.g., isotonic saline, ACD, or platelet additive solutions). In one embodiment of washing, modified platelets are washed using an excess of a washing buffer consisting of a 1:1 ratio of phosphate buffered saline and ACD at physiologic pH (pH 7-7.8). The platelet-wash solution is mixed gently (e.g., inverting the tube of platelet-wash solution several times) followed by centrifugation at 600 g for 3 minutes. Following washing, the wash supernatant is removed. Platelet counts are determined via automated cell counters and the platelets are resuspended to the desired modified platelet count per unit volume using physiologic solutions (e.g., plasma, saline, platelet additive solutions). At this point, the platelets are suitable for storage at <20° C. and/or experimental or clinical usage. In other embodiments, the washing step is automated using clinical cell washers.

In other preparation embodiments, the source of platelets can be whole blood, leukoreduced whole blood, whole blood derived buffy coat platelets or apheresis platelets. Alternatively for non-clinical or veterinary use, a wide range of other platelet preparations (e.g., purified platelets obtained using magnetic bead technology, cell culture and expansion, or via cell sorter technology) can be similarly derivatized. Platelet concentration can also be significantly varied relative to the PEG or PEG-derivative concentration and/or physiologic media.

Depending on the PEG/PEG derivative and the linker group used in the preceding methodology for forming modified platelets, either: (1) the associated linker molecule may remain part of the final structure of the polymerated chemical (as in the polymerated chemical 59 of FIG. 2; e.g., cyanuric chloride activated mPEG); or (2) the linker group may mediate the chemical reaction between PEG/PEG derivative and a protein of the platelet membrane but nonetheless function as a leaving group so that the associated linker molecule is not part of the final structure of the polymerated chemical (as in the polymerated chemical 89 of FIG. 2; e.g., benzotriazole cabonate activated mPEG).

As described supra, the present invention fulfills a long-felt, unsatisfied need in transfusion medicine to store platelets under cooling temperature conditions by inhibiting microbial growth while maintaining acceptable platelet function and viability. The current invention addresses this long-felt, unsatisfied need, by covalently modifying the platelet membrane with PEG or a PEG derivative (FIG. 4). As a consequence of this covalent modification of the platelet membrane, the detrimental effects of cold storage/exposure are inhibited/prevented as evidenced by: maintenance of/return to normal platelet morphology upon transition from 4° to >15° C. (FIGS. 5 and 6); prevention of platelet microaggregation (FIGS. 5 and 6); attenuation of cold storage activation of platelets during storage (FIG. 7); maintenance of normal platelet activation and clot formation upon stimulation (FIGS. 8 and 9); and inhibition and/or attenuation of GP1b clustering and immunologic recognition of platelet surface proteins (FIGS. 4 and 7).

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A platelet structure, comprising:
   at least one modified platelet at a temperature below 20° C., each modified platelet comprising a platelet and at least one polymerated chemical, each polymerated chemical either comprising a polymer covalently bonded directly to the platelet membrane of the platelet or comprising the polymer and a linker molecule such that the linker molecule is covalently bonded to the platelet membrane of the platelet and the polymer is covalently attached to the linker molecule, the polymer of each polymerated chemical of each modified platelet being independently selected from the group consisting of polyethylene glycol (PEG) and a PEG derivative, said at least one modified platelet not comprising a modification of the platelet membrane of each platelet with a glycan-modifying agent.

2. The structure of claim 1, wherein if the at least one modified platelet were subsequently introduced into a mammal, the at least one modified platelet would have normal platelet functionality in the mammal.

3. The structure of claim 1, wherein the temperature is in a temperature range from 0° C. to below 20° C.

4. The structure of claim 1, wherein the temperature is in a temperature range from 4° C. to 14° C.

5. The structure of claim 1, wherein the modified platelets are in a platelet additive.

6. The structure of claim 1, wherein a polymer of a polymerated chemical of a modified platelet of the at least one modified platelet consists of PEG.

7. The structure of claim 1, wherein a polymer of a polymerated chemical of a modified platelet of the at least one modified platelet consists of a PEG derivative.

8. The structure of claim 1, wherein the at least one modified platelet consists of a plurality of modified platelets, wherein a polymer of a polymerated chemical of a first modified platelet of the plurality of modified platelets consists of a first PEG derivative, and wherein a polymer of a polymerated chemical of either the first modified platelet or a second modified platelet of the plurality of modified platelets consists of a second PEG derivative that differs from the first PEG derivative.

9. A method for storing platelets, comprising:
   forming the platelet structure of claim 1, said forming comprising storing the at least one modified platelet in a temperature range below 20° C. for a time period of at least one hour.

10. The method of claim 9, wherein the temperature range is from 0° C. to below 20° C.

11. The method of claim 9, wherein the temperature range is from 4° C. to 14° C.

12. The method of claim 9, wherein the time period exceeds 5 days.

13. The method of claim 9, wherein said storing comprises storing the at least one modified platelet in a platelet additive solution within the temperature range for the time period.

14. The method of claim 9, further comprising prior to said forming the at least one modified platelet: preparing the at least one platelet using whole blood-derived platelet rich plasma (PRP) platelets, whole blood-derived huffy coat platelets, or apheresis platelets.

15. The method of claim 9, wherein a polymer of a polymerated chemical of a modified platelet of the at least one modified platelet consists of PEG.

16. The method of claim 9, wherein a polymer of a polymerated chemical of a modified platelet of the at least one modified platelet consists of a PEG derivative.

17. The method of claim 9, wherein the at least one modified platelet consists of a plurality of modified platelets, wherein a polymer of a polymerated chemical of a first modified platelet of the plurality of modified platelets consists of a first PEG derivative, and wherein a polymer of a polymerated chemical of either the first modified platelet or a second modified platelet of the plurality of modified platelets consists of a second PEG derivative that differs from the first PEG derivative.

18. The method of claim 9, wherein if after said storing is perfoiined the at least one modified platelet were introduced into the mammal, then the at least one modified platelet introduced into the mammal would have a longer increased circulation half-life in the mammal than would a same number of non-modified platelets introduced into the mammal after being stored in the temperature range for the time period.

19. The method of claim 9, wherein said storing the at least one modified platelet in the temperature range below 20° C. for the time period prevents and/or retards microbial growth on the stored platelets during the time period.

20. The method of claim 9,
   wherein each platelet in the at least one modified platelet had been obtained from a mammal prior said forming;
   wherein after said storing has been performed, the at least one modified platelet has a post-transfusion resting morphology recovery in the mammal of 50% to 80%, relative to fresh platelets from the mammal, at a post-transfusion time in a range of 1 hour to 24 hours measured from a time of transfusion of the at least one modified platelet and the fresh platelet into the mammal; and
   wherein the at least one modified platelet consists of at least N platelets, N being a minimum number of modified platelets necessary for a determination of the post-transfusion resting morphology recovery to have a statistical error not exceeding a specified threshold percent in a range of 1% to 20%.

21. The method of claim 9,
   wherein each platelet in the at least one modified platelet had been obtained from a mammal prior said forming;
   wherein after said storing has been performed, the at least one modified platelet has a post-transfusion survival in the mammal of 30% to 70%, relative to fresh platelets from the mammal, at a post-transfusion time in a range of 1 hour to 24 hours measured from a time of transfusion of the at least one modified platelet and the fresh platelet into the mammal; and
   wherein the at least one modified platelet consists of at least N platelets, N being a minimum number of modified platelets necessary for a determination of the post-transfusion survival to have a statistical error not exceeding a specified threshold percent in a range of 1% to 20%.

22. A method for using platelets, comprising:
   forming the platelet structure of claim 1, said forming comprising storing the at least one modified platelet in a temperature range below 20° C. for a time period of at least one hour; and
   after said storing, introducing the at least one modified platelet into a mammal.

23. The method of claim 22, wherein the mammal is a human being.

24. The method of claim 22, wherein the mammal is a non-human mammal.

25. The method of claim 22, wherein the temperature range is from 0° C. to below 20° C.

26. The method of claim 22, wherein the temperature range is from 4° C. to 14° C.

27. The method of claim 22, wherein the time period exceeds 5 days.

28. The method of claim 22, wherein a polymer of a polymerated chemical of a modified platelet of the at least one modified platelet consists of PEG.

29. The method of claim 22, wherein a polymer of a polymerated chemical of a modified platelet of the at least one modified platelet consists of a PEG derivative.

30. The method of claim 22, wherein the at least one modified platelet consists of a plurality of modified platelets, wherein a polymer of a polymerated chemical of a first modified platelet of the plurality of modified platelets consists of a first PEG derivative, and wherein a polymer of a polymerated chemical of either the first modified platelet or a second modified platelet of the plurality of modified platelets consists of a second PEG derivative that differs from the first PEG derivative.

31. The method of claim 22, wherein the introduced at least one modified platelet has a longer increased circulation half-life in the mammal than would a same number of non-modified platelets introduced into the mammal after being stored in the temperature range for the time period.

32. The method of claim 22,
wherein each platelet in the at least one modified platelet had been obtained from an animal prior to formation of the at least one platelet;
wherein the animal is the mammal or another mammal;
wherein the at least one modified platelet, after having been stored in the temperature range for the time period and before said introducing is performed, has a post-transfusion resting morphology recovery in the animal of 50% to 80%, relative to fresh platelets from the animal, at a post-transfusion time in a range of 1 hour to 24 hours measured from a time of transfusion of the at least one modified platelet and the fresh platelets into the animal; and
wherein the at least one modified platelet consists of at least N platelets, N being a minimum number of modified platelets necessary for a determination of the post-transfusion resting morphology recovery to have a statistical error not exceeding a specified threshold percent in a range of 1% to 20%.

33. The method of claim 22,
wherein each platelet in the at least one modified platelet had been obtained from an animal prior to formation of the at least one platelet;
wherein the animal is the mammal or another mammal;
wherein the at least one modified platelet, after having been stored in the temperature range for the time period and before said introducing is performed, has a post-transfusion survival in the animal of 30% to 70%, relative to fresh platelets from the animal, at a post-transfusion time in a range of 1 hour to 24 hours measured from a time of transfusion of the at least one modified platelet and the fresh platelets into the animal; and
wherein the at least one modified platelet consists of at least N platelets, N being a minimum number of modified platelets necessary for a determination of the post-transfusion survival to have a statistical error not exceeding a specified threshold percent in a range of 1% to 20%.

* * * * *

UNITED STATES PATENT AND TRADEMARK OFFICE
CERTIFICATE OF CORRECTION

PATENT NO.       : 7,964,339 B2                                      Page 1 of 1
APPLICATION NO.  : 11/673287
DATED            : June 21, 2011
INVENTOR(S)      : Mark D. Scott et al.

It is certified that error appears in the above-identified patent and that said Letters Patent is hereby corrected as shown below:

in column 11, line 66, claim 14, "huffy coat" should read --buffy coat--;
in column 12, line 18, claim 18, "perfoiined" should read --performed--.

Signed and Sealed this
Twentieth Day of September, 2011

David J. Kappos
*Director of the United States Patent and Trademark Office*